United States Patent
King et al.

(10) Patent No.: US 11,037,678 B2
(45) Date of Patent: *Jun. 15, 2021

(54) MEDICAL DEVICE WITH INTERFACES FOR CAPTURING VITAL SIGNS DATA AND AFFIRMATIVELY SKIPPING PARAMETERS ASSOCIATED WITH THE VITAL SIGNS DATA

(71) Applicant: Welch Allyn, Inc., Skaneateles Falls, NY (US)

(72) Inventors: Catherine M. King, Ithaca, NY (US); Thomas A. Myers, Syracuse, NY (US); Shawn C. St. Pierre, Syracuse, NY (US); Gregory P. Vassallo, Manlius, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 249 days.

This patent is subject to a terminal disclaimer.

(21) Appl. No.: 15/669,568

(22) Filed: Aug. 4, 2017

(65) Prior Publication Data

US 2017/0329920 A1 Nov. 16, 2017

Related U.S. Application Data

(63) Continuation of application No. 14/535,534, filed on Nov. 7, 2014, now Pat. No. 9,763,629.

(51) Int. Cl.
*G06F 3/01* (2006.01)
*G06F 3/0488* (2013.01)
(Continued)

(52) U.S. Cl.
CPC ............. *G16H 40/63* (2018.01); *A61B 5/742* (2013.01); *A61B 5/7475* (2013.01); *G16H 10/60* (2018.01);
(Continued)

(58) Field of Classification Search
CPC ........ G16H 50/30; G16H 40/63; G16H 10/60; G16H 15/00; G16H 40/67; A61B 5/7475; A61B 5/742
See application file for complete search history.

(56) References Cited

U.S. PATENT DOCUMENTS 6,188,407 B1 2/2001 Smith et al.
6,458,081 B1 10/2002 Matsui et al.
(Continued)

OTHER PUBLICATIONS

International Search Report and Written Opinion in PCT/US2015/059505, dated Feb. 29, 2016, 15 pages.

*Primary Examiner* — Abdullah Al Kawsar
*Assistant Examiner* — Kenny Nguyen
(74) *Attorney, Agent, or Firm* — Merchant & Gould P.C.

(57) ABSTRACT

A method for displaying information and receiving inputs with a medical device includes displaying a first interface on a display of the medical device, receiving various inputs from a user, displaying a second interface on the display of the medical device, and receiving vital signs data from the patient using the second interface. The first interface includes a login area including one or more prompts for information identifying a user of the medical device and profile selection area including two or more profiles offered by the medical device. The method further involves receiving user identifying information from the user via the login area, confirming the user identifying information, activating the profile selection area in response to confirming the user identifying information, receiving a profile selection from the user via the profile selection area, and receiving patient identification information from the user with the medical device.

16 Claims, 15 Drawing Sheets

(51) Int. Cl.
*G16H 40/63* (2018.01)
*A61B 5/00* (2006.01)
*G16H 15/00* (2018.01)
*G16H 50/30* (2018.01)
*G16H 10/60* (2018.01)
*G16H 40/67* (2018.01)

(52) U.S. Cl.
CPC ............ *G16H 15/00* (2018.01); *G16H 50/30* (2018.01); *G16H 40/67* (2018.01)

(56) References Cited

U.S. PATENT DOCUMENTS

| | | | |
|---|---|---|---|
| 7,778,851 B2 | 8/2010 | Schoenberg et al. | |
| 8,788,502 B1* | 7/2014 | Hensel | G06F 16/951 |
| | | | 707/738 |
| 8,832,558 B2 | 9/2014 | Cardarelli | |
| 8,843,647 B1 | 9/2014 | Sandoval | |
| 2004/0059672 A1* | 3/2004 | Baig | G06Q 20/04 |
| | | | 705/40 |
| 2006/0229557 A1* | 10/2006 | Fathallah | G06F 19/00 |
| | | | 604/131 |
| 2007/0135730 A1 | 6/2007 | Cromwell | |
| 2007/0138069 A1 | 6/2007 | Roncadi et al. | |
| 2007/0143215 A1* | 6/2007 | Willems | G16H 10/65 |
| | | | 705/51 |
| 2007/0185390 A1* | 8/2007 | Perkins | A61B 5/0002 |
| | | | 600/300 |
| 2007/0260995 A1 | 11/2007 | Stienhans | |
| 2008/0071251 A1* | 3/2008 | Moubayed | A61M 5/172 |
| | | | 604/890.1 |
| 2008/0262870 A1* | 10/2008 | Jones | G16H 40/63 |
| | | | 705/2 |
| 2009/0300620 A1 | 12/2009 | Park et al. | |
| 2009/0313549 A1 | 12/2009 | Casner et al. | |
| 2010/0131293 A1 | 5/2010 | Linthicum et al. | |
| 2010/0235782 A1 | 9/2010 | Powell | |
| 2011/0029865 A1 | 2/2011 | Gilland et al. | |
| 2011/0072416 A1* | 3/2011 | Hudson, Jr. | G06F 8/38 |
| | | | 717/122 |
| 2011/0179361 A1 | 7/2011 | Cardarelli et al. | |
| 2013/0044111 A1 | 2/2013 | VanGilder et al. | |
| 2013/0267793 A1* | 10/2013 | Meador | A61B 5/0205 |
| | | | 600/301 |
| 2013/0267861 A1 | 10/2013 | Vassallo et al. | |
| 2013/0283197 A1 | 10/2013 | Skidmore | |
| 2013/0311927 A1* | 11/2013 | Grossman | G06Q 10/10 |
| | | | 715/771 |
| 2014/0207675 A1* | 7/2014 | Rosendahl | G06F 7/00 |
| | | | 705/44 |
| 2015/0012301 A1* | 1/2015 | Weschler | G16H 10/60 |
| | | | 705/3 |
| 2015/0100877 A1* | 4/2015 | Long | G06F 9/542 |
| | | | 715/234 |
| 2015/0170108 A1* | 6/2015 | Kim | G06Q 10/1097 |
| | | | 705/7.21 |
| 2016/0119313 A1* | 4/2016 | Zhang | H04L 63/083 |
| | | | 726/6 |
| 2016/0128646 A1 | 5/2016 | King et al. | |

* cited by examiner

FIG. 12

Custom score summary — 3 of 3

Aquired vitals

- [0] NIBP – Systolic  132 mmHg
- [0] Temperature  99.7 °F
- [0] Pulse rate  63 BPM
- [0] SpO2  99 %
- [0] Consciuos level  Alert
- [0] Glucose  126

Required response:
Protocol does not require further action

Total MEWS score: 0

[OK]

MEDICAL DEVICE WITH INTERFACES FOR CAPTURING VITAL SIGNS DATA AND AFFIRMATIVELY SKIPPING PARAMETERS ASSOCIATED WITH THE VITAL SIGNS DATA

CROSS-REFERENCE TO RELATED APPLICATIONS

This application is a continuation of U.S. patent application Ser. No. 14/535,534, filed Nov. 7, 2014, entitled, "Medical device with context-specific interfaces." The disclosure of this priority application is hereby incorporated by reference in its entirety into the present application.

BACKGROUND

As the amount of information that is captured by a medical device increases, the complexity of using the device also increases. Such use can be complicated by a failure to understand how the device is currently configured to operate. Further, a user can be confused about what information is needed to complete a medical record. Such complexities can make the use of the medical device more difficult and undermine the efficiencies associated with the electronic capture and retention of medical data.

SUMMARY

In one aspect, a medical device includes: a processor; a display; and memory encoding instructions that, when executed by the processor, cause the processor to create an interface on the display, the interface including: a login area including one or more prompts for information identifying a user of the medical device; and a profile selection area including two or more profiles offered by the medical device, wherein each of the profiles is a series of tasks to be performed by the medical device, and a description of each profile is provided in the profile selection area.

In another aspect, a medical device includes: a processor; a display; and memory encoding instructions that, when executed by the processor, cause the processor to create an interface on the display, the interface including: a vital signs area programmed to display data associated with a plurality of vital signs for a patient; and an additional parameters area programmed to capture one or more additional parameters associated with the vital signs displayed in the vital signs area.

In yet another aspect, a medical device includes: a processor; a display; and memory encoding instructions that, when executed by the processor, cause the processor to create an interface on the display, the interface including: a login area including one or more prompts for information identifying a user of the medical device; a profile selection area including two or more profiles offered by the device, wherein each of the profiles is a series of tasks to be performed by the medical device, and a description of each profile is provided in the profile selection area; a vital signs area programmed to display a plurality of vital signs associated with a patient; and an additional parameters area programmed to capture one or more additional parameters associated with the vital signs displayed in the vital signs area.

DESCRIPTION OF THE FIGURES

FIG. 12 illustrates another view of the interface of FIG. 9.

DETAILED DESCRIPTION

Examples of ambulatory care environments can include hospitals, clinics, managed care facilities, and other locations where medical care is provided. Medical personnel in ambulatory care environments can utilize vital signs monitoring devices, vital signs displays, personal computing devices and electronic medical record access portals. Medical staff and providers often need to record a patient's vital signs and enter those vital signs into the patient's electronic medical record. Currently, providers must perform vital signs measurements, remember the measurements, and then enter those measurements into one or more computing devices which may or may not be directly linked to the patient's electronic medical record.

Figure 1:
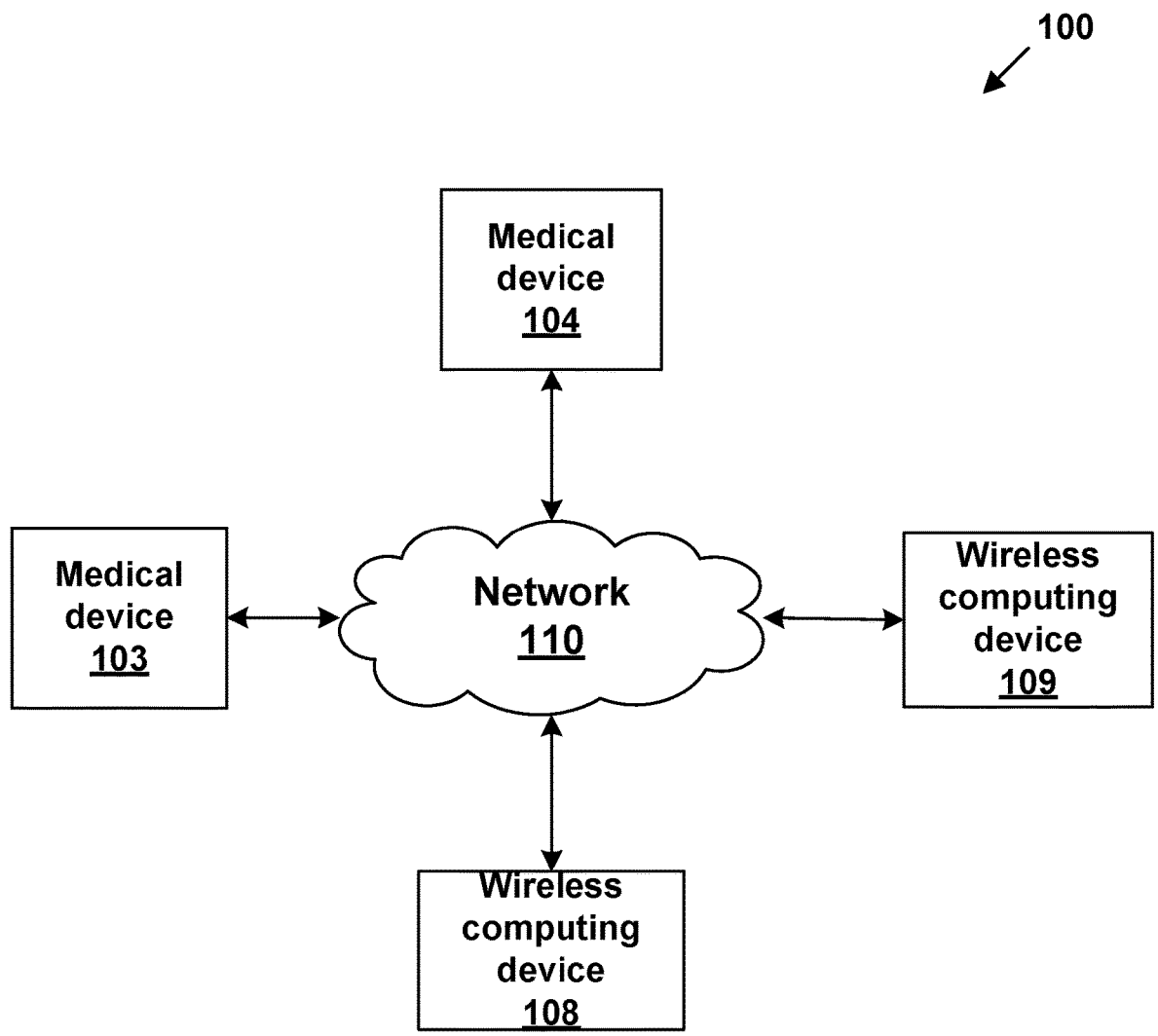
FIG. 1 illustrates a block diagram of a wireless ambulatory care system.

FIG. 1 illustrates a block diagram of an example wireless ambulatory care network 100. The example network 100 includes medical devices 103 and 104, wireless computing devices 108 and 109, and communication network 110. In embodiments, the example network 100 can include more or fewer medical devices 103 and 104. In embodiments, the example network can include more or fewer wireless computing devices 108 and 109. The communication network 110 can be a wireless network, such as WiFi, Bluetooth, Zigbee, Ant, Z-Wave, etc.

In some embodiments, the one or more medical devices 103 and 104 can include one or more vital signs measurement components. For example, the medical devices 103 can include, for example, a thermometer, a heart rate monitor, a pulse oximeter, a non-invasive blood pressure monitor, and a respiration rate monitor. In embodiments, one or more vital signs measurement components are wirelessly linked to the medical devices 103 and 104 and can transmit measurements to the medical devices 103 and 104.

Example computing components of medical devices 103 and 104 are shown and described in more detail with reference to FIG. 15, below.

In some embodiments, the one or more wireless computing devices 108 and 109 can be smart phones, tablet computers, personal digital assistants, laptop computers, and desktop computers, which can optionally be mounted on portable carts. Example computing components of the one or more wireless computing devices 108 and 109 are shown and described in more detail with reference to FIG. 15, below. The use of less complicated wireless computing devices 108 and 109, such as heart rate monitors, pulse oximeters, etc., is also contemplated by this document.

Figure 2:
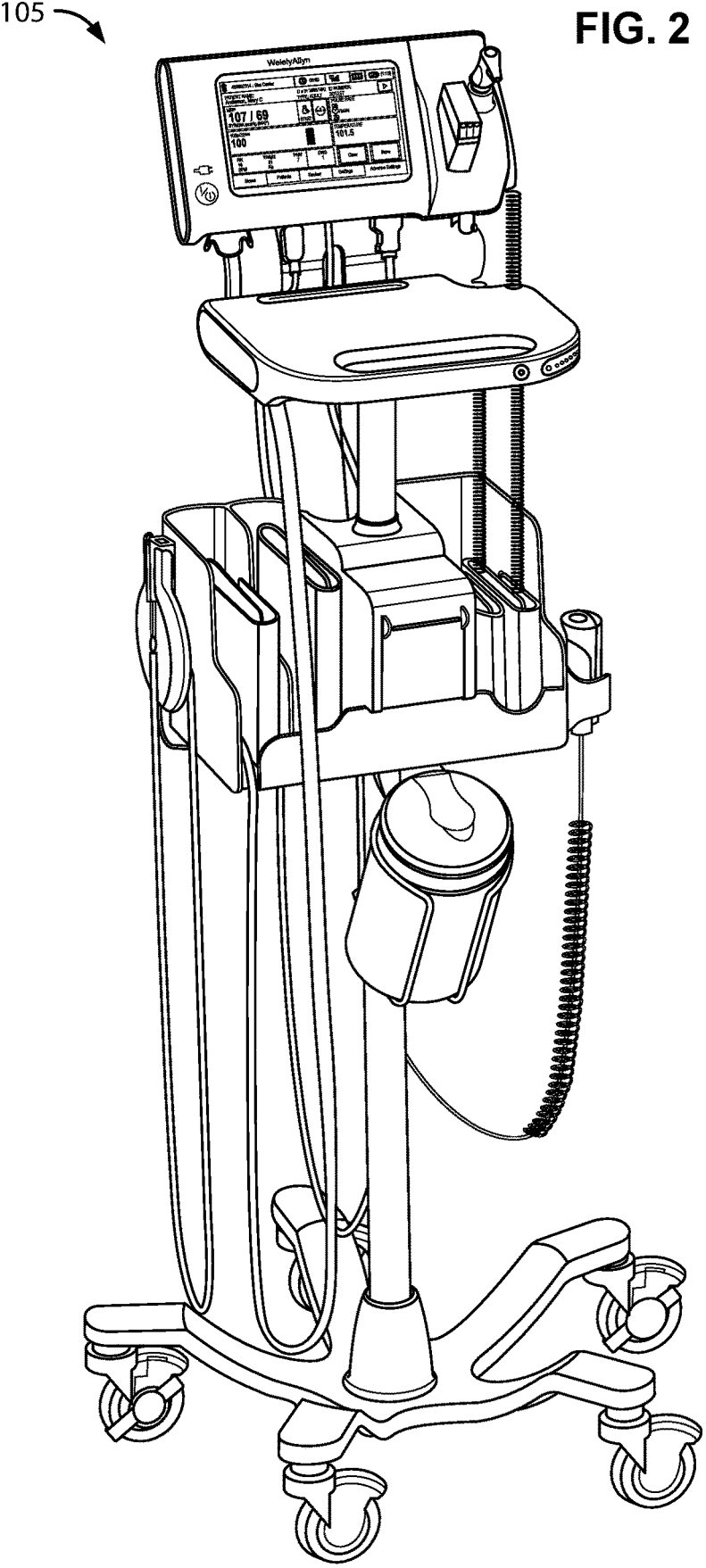
FIG. 2 illustrates an example medical device of the system of FIG. 1.
Figure 3:
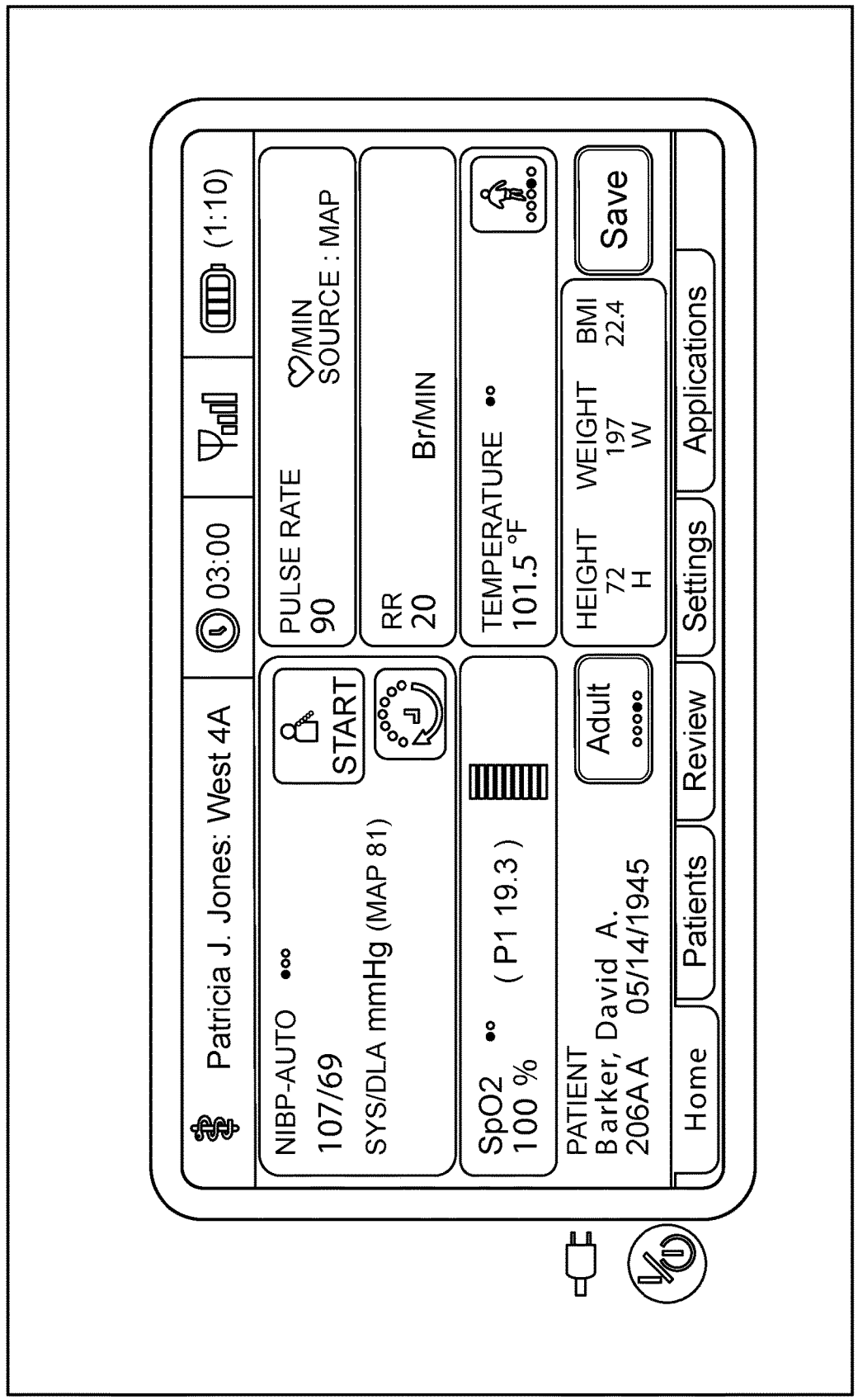
FIG. 3 illustrates another example medical device of the system of FIG. 1.

FIG. 2 illustrates one example of the medical device 105. The medical device 105 is shown on a mobile cart, and the medical device 105 is programmed to provide the functionalities described herein. The medical device 105 includes a user interface, such as a touch screen, and includes the ability to execute multiple workflows or profiles. In some embodiments, the medical devices 105 and 106 in FIGS. 2 and 3 are the medical device 103 or 104 shown in, and described with reference to, FIG. 1. Other embodiments can include more or fewer components than those shown in FIG. 2, or include different components that accomplish the same or a similar function.

The medical device 105 is able to operate within one or more profiles. A profile is a series of one or more tasks that a user of the medical device 105 performs. When the medical device 105 operates within a profile, the medical device 105 provides functionality suitable for assisting the user in performing the profile. When the medical device 105 operates within different profiles, the medical device 105 provides different functionality.

When the medical device 105 is manufactured, the medical device 105 is configured to be able to operate within one or more profiles. After the medical device 105 is manufactured, the medical device 105 can be reconfigured to operate within one or more additional profiles. In this way, a user can adapt the medical device 105 for use in different profiles as needed.

In various embodiments, the medical device 105 operates within various profiles. For example, in some embodiments, the medical device 105 can operate within a monitoring profile or a non-monitoring profile. Example types of non-monitoring profiles include, but are not limited to, a spot check profile and an office profile. An example of a monitoring profile includes, but is not limited to, an intervals profile.

An additional example of the medical device 106 is shown in FIG. 3. In this example, the medical device 106 is similar to that of the medical device 105 described above. In embodiments, the medical device 106 is mounted on a wall. The medical device 106 is programmed in a manner similar to that described above to monitor physiological parameters of a patient. In some embodiments, the medical device 106 is a stand-alone device, which can mean that is not part of a mobile cart and it is not part of a wall-mounted station.

In the examples described herein, the medical devices 104, 105, 106 are computing devices that have been programmed to perform special, complex functions. These specially-programmed devices function to manipulate and provide data to the users in an improved form factor and with greater efficiency.

For example, as described further below, the medical devices 104, 105, 106 are specially programmed to provide the user with an improved interface during initial use of the devices. This allows the user to more efficiently select a profile for controlling the functionality of the device.

In addition, the medical devices 104, 105, 106 are specially programmed to assist the users once vital signs information is captured from the patients. For example, the devices are programmed to more efficiently and easily capture additional contextual information that is needed when saving vital signs data to a permanent record, such as an EMR record. This is accomplished using an interface that is more intuitive and robust.

Referring now to FIGS. 4-8, an example interface 200 for allowing a user to login to and select a profile for the medical devices 104, 105, 106 is shown.

Figure 4:
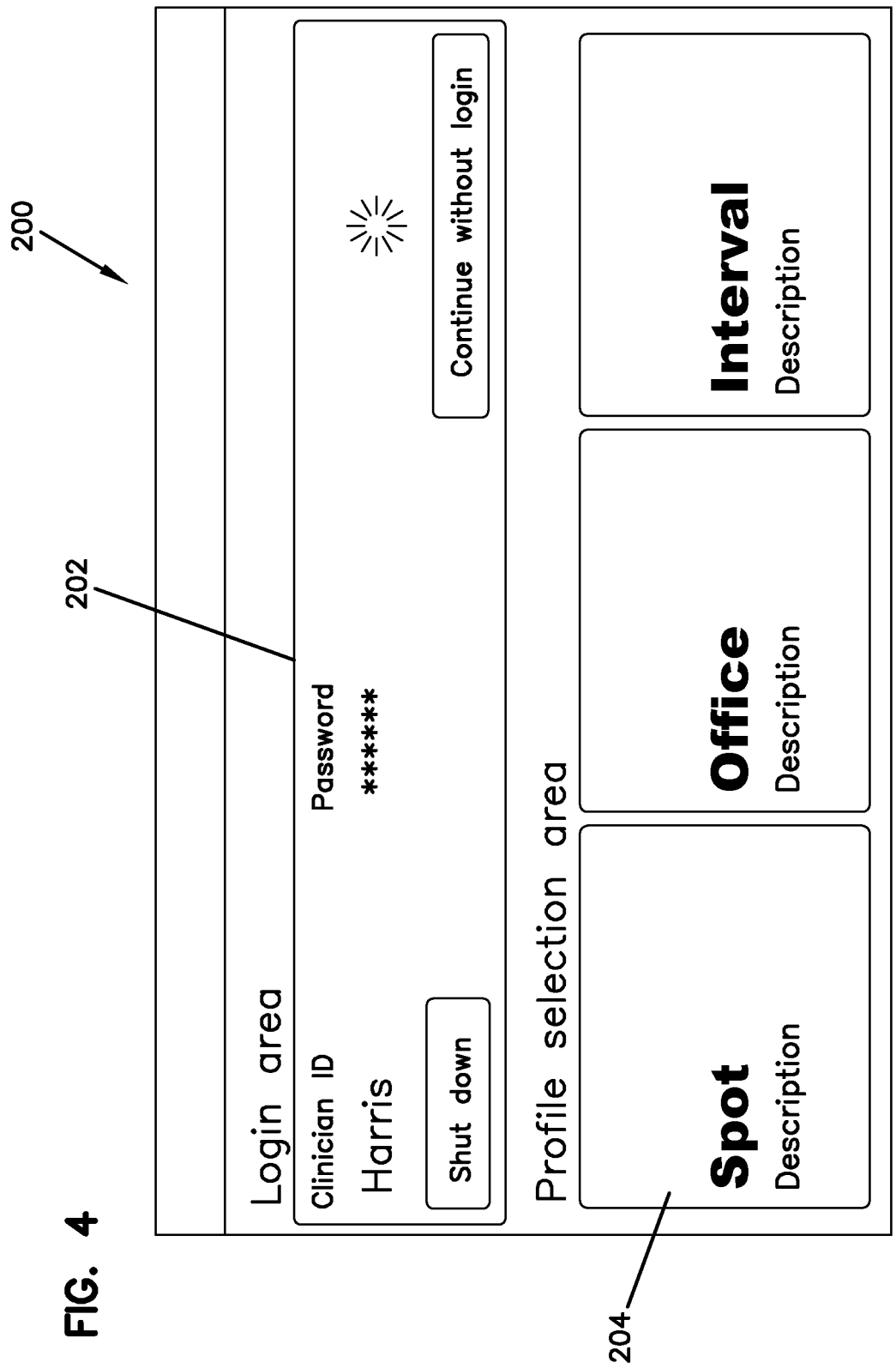
FIG. 4 illustrates an example login and profile selection interface for the medical device of FIG. 3.

In FIG. 4, the interface 200 includes a login area 202 and a profile selection area 204. The login area 202 collects information to assist in the identification of the user. This information includes a clinician identifier (ID) and a password. In other examples, different information can be collected, such as a user name or badge number. Any other identification information can also be captured as desired. The user can enter the identification information into the device using an input device such as a keyboard, touchscreen, mouse, scanner, etc.

Figure 5:
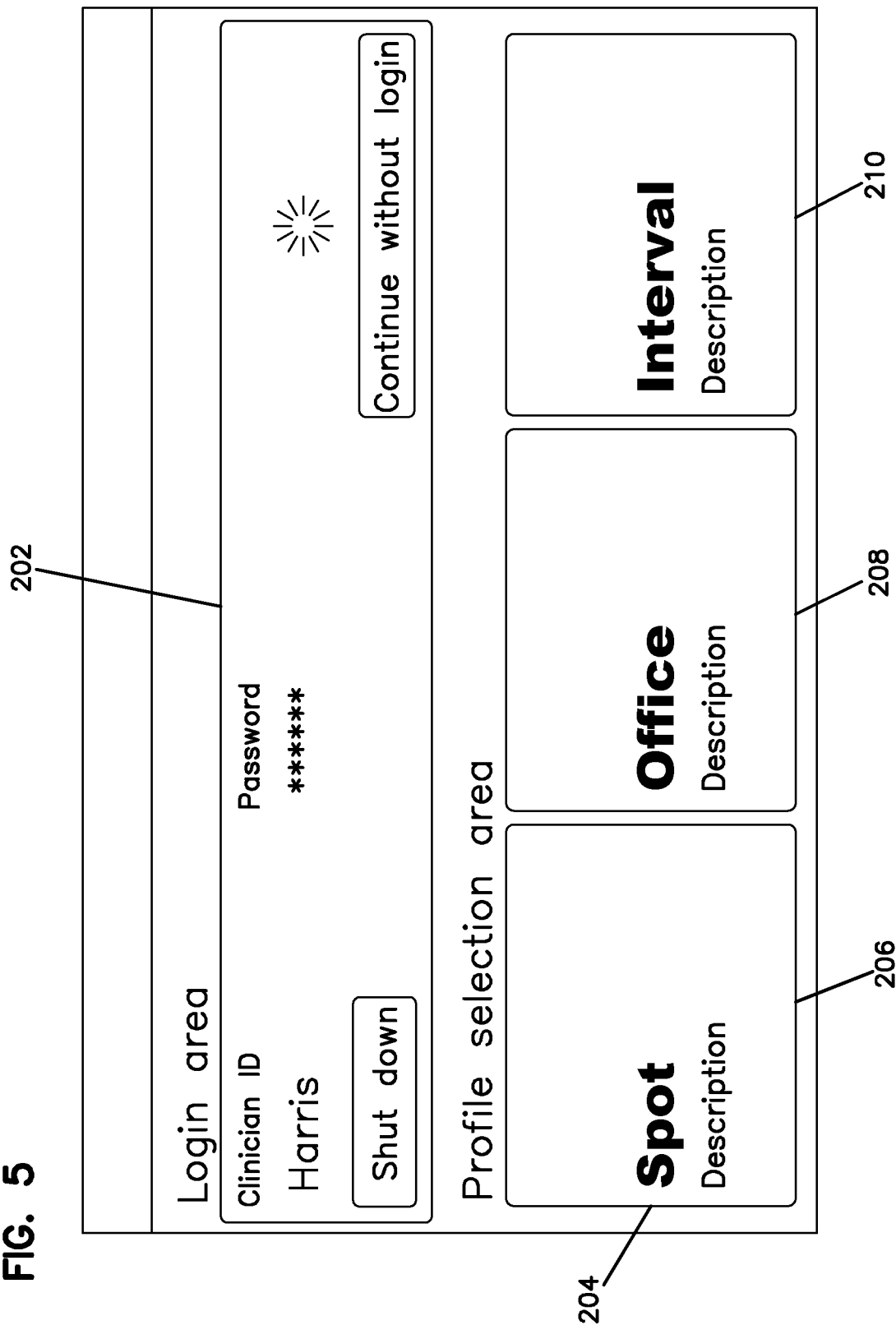
FIG. 5 illustrates another view of the interface of FIG. 4.

Referring now to FIG. 5, once the user's identification information (i.e., clinician ID and password) is provided, the device confirms the credentials. This can be completed locally (i.e., by the device itself) and/or by accessing information on the network 110.

Figure 6:
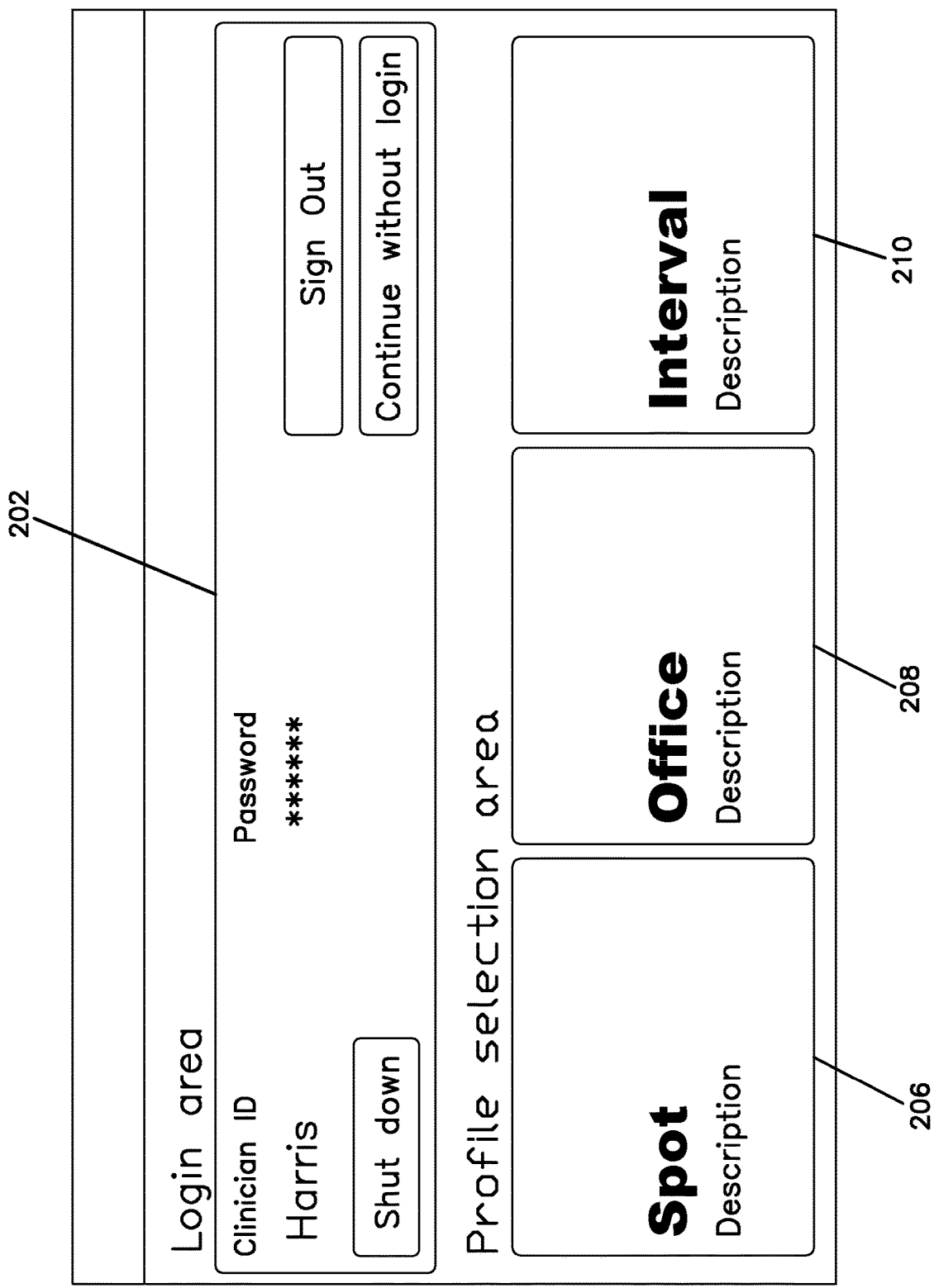
FIG. 6 illustrates another view of the interface of FIG. 4.

In FIG. 6, the user's identification information has been confirmed. At this point, the profile selection area 204 is now active. The profile selection area 204 generally provides information about the different profiles that can be implemented by the device. In the example given, the device can operate using one of three profiles: spot, office, or interval.

Each of the profiles includes a separate area 206, 208, 210 that allows for contextual information to be provided about that profile. For example, the spot area 206 includes the name of the profile and a description of what is accomplished using the profile. This description can include such information as: (i) data acquisition—what vital signs data is collected for the profile; (ii) data retention—how that vital signs data is stored, such as in duration; (iii) patient identification retention—how patient-specific information is retained by the device; etc. In some examples, the description is a textual string (e.g., a series of sentences and/or one or more paragraphs) that describe, in prose form, how the profile functions.

In this example, the spot profile is a non-monitoring profile, and the description can provide information to the user such as: a customized label describing the facility's preferred term for the workflow such as "Rounds", "Vitals", "Observations", a customized description such as, "For single-reading use on multiple patients," or "Multiple patients per round", and a customized icon to provide visual recognition of the workflow. Similar language can be provided in the office area 208 (e.g., a customized label describing the facility's preferred term for the workflow such as "Vitals", "Exams", or "Readings", a customized description such as, "For use on routine exams", and a customized icon to provide visual recognition of the workflow) and interval area 210 (e.g., a customized label describing the facility's preferred term for the workflow such as "Interval Monitoring", "Intervals", "Bedside Observations", a customized description such as, "For multiple readings on single patients" or "Single patient monitoring", and a customized icon to provide visual recognition of the workflow) to allow the user to make an educated decision on how to configure the device before the device is used. The user can select one of the areas 206, 208, 210 as desired using an input device (e.g., keyboard, mouse or touch) to start the device in that profile.

Figure 7:
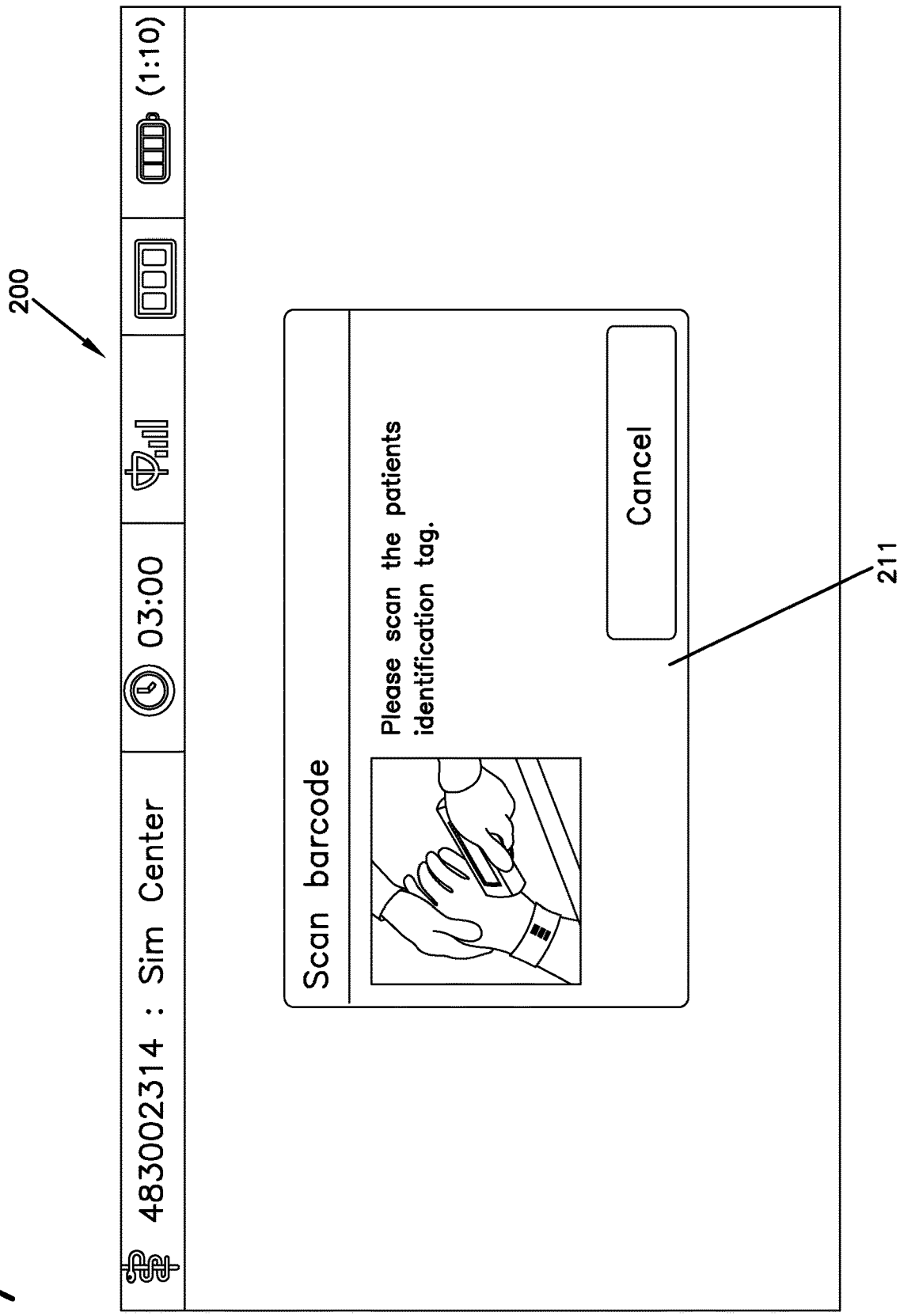
FIG. 7 illustrates another view of the interface of FIG. 4.
Figure 8:
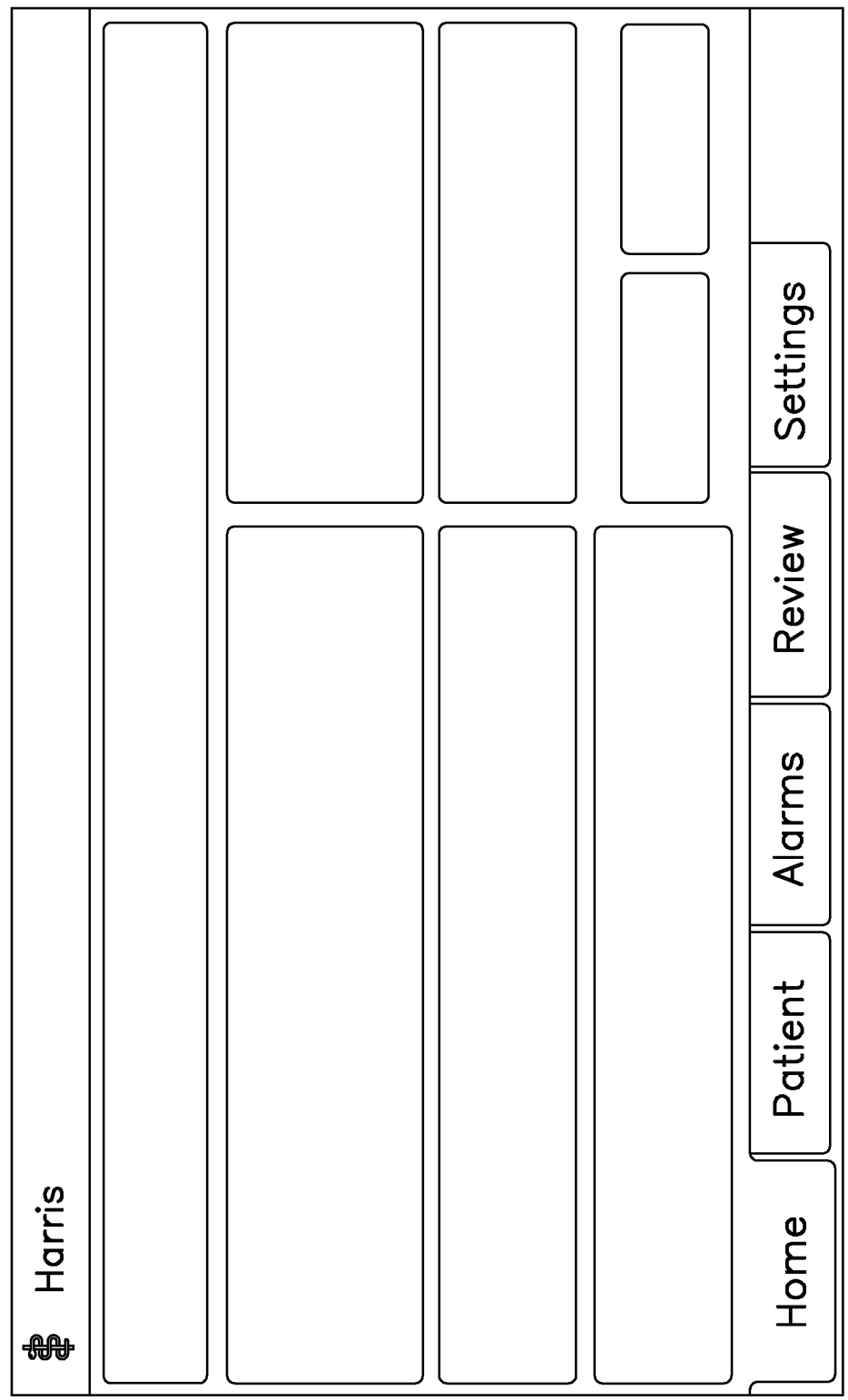
FIG. 8 illustrates an example vital signs interface for the medical device of FIG. 3.

In FIG. 7, once the profile is selected, the user must identify the patient. In this example, a box 211 is presented to the user, and the user can identify the patient using various methods, such as by scanning a patient identification tag.

Once the profile is selected and the patient is identified, the user is provided with an interface 220, as shown in FIG.

8. This interface 220 can be used to capture vital signs information, such as that shown in FIGS. 2-3.

In the example shown, more or fewer profile areas can be shown. In some embodiments, the profile areas are configurable depending on the type of device and/or the type of use for the device. For example, a particular facility (e.g., hospital or clinic) can tailor the profiles to those used at that facility, as well as tailor the description of those profiles to use vernacular that is more easily understood at the given facility. In this manner, the user is provided with the relevant profiles, and each profile area provides additional context so that the user can make the proper selection of the desired profile before vital capture.

In the shown embodiment, the login area 202 includes a control ("Continue without login") that allows a user to use the medical device without providing login credentials. Such functionality could be used, for example, in an emergency situation where the time required to provide those credentials could compromise patient health. However, if the medical device is accessed in this manner, some of the functionality of the medical device can be limited or otherwise modified. For example, the medical device may not allow any vital signs data to be recorded to an EMR until the user provides the necessary credentials. Other configurations are possible.

Referring now to FIGS. 9-14, an example interface 320 for capturing additional data upon saving of vital signs information by the medical devices 104, 105, 106 is shown. In these examples, the additional data can include parameters associated with the vitals data that is collected and stored by the medical device. Examples of this data include inputs for text, integers, decimals, lists, and modifiers (a custom input becomes a modifier if an association is established between the input and a parameter on the device during configuration). All custom inputs can have input ranges specified and validation rules established. Example custom inputs include, without limitation, Capillary Refill Time (CRT), Glucose, Glasgow Coma Score, Urine Output, Cuff Size, O2 Flow Rate, O2 concentration, Measurement Site, etc. The interface 320 allows for the sequential capture of this information in an easy-to-use and efficient manner.

Figure 9:
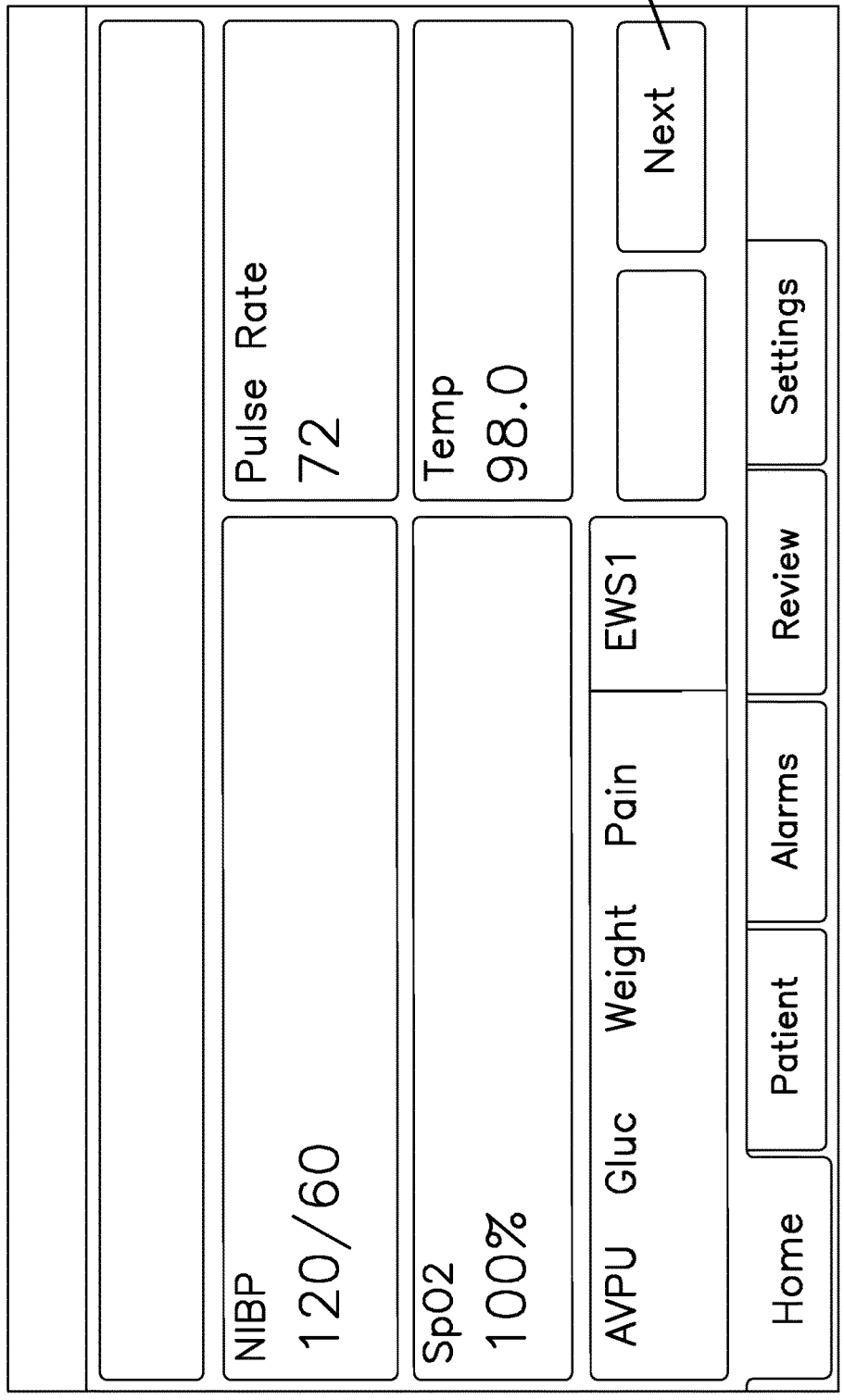
FIG. 9 illustrates an example interface for the medical device of FIG. 3.

At FIG. 9, the interface 320 is shown displaying captured vital signs data, including NIBP, Pulse Rate, SpO2, and Temperature. As noted, these are only examples, and other vital signs data can also be captured and displayed. Once capture of the vital signs data is complete, the user selects a next button 328 to record the vital signs data to, for example, an EMR.

Figure 10:
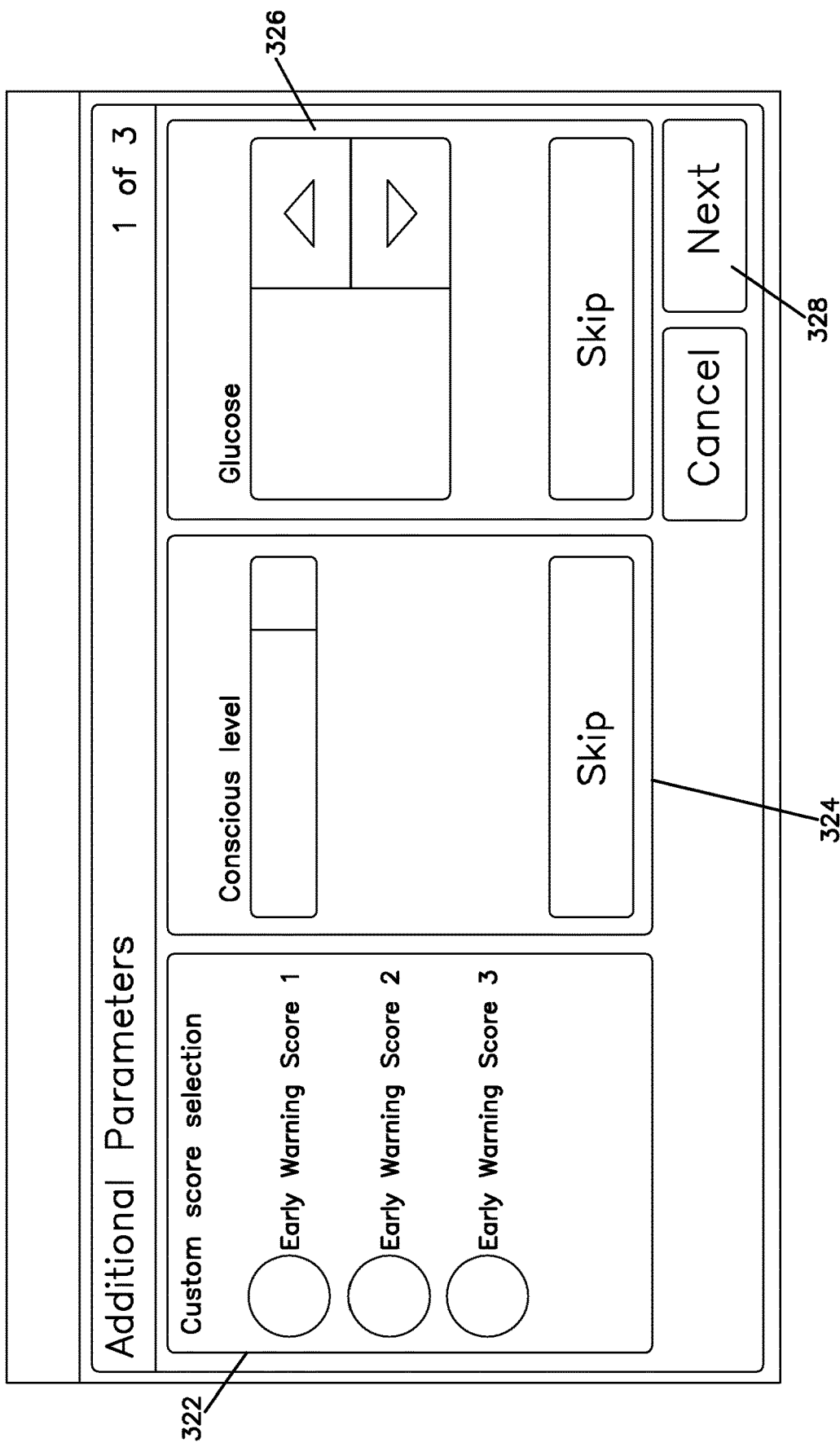
FIG. 10 illustrates another view of the interface of FIG. 9.

FIG. 10 shows additional parameters areas 322, 324, 326 that are displayed when the user selects the next button 328 on the interface 320. These additional parameter areas 322, 324, 326 are used to capture further information that is needed when recording the vital signs data to the EMR.

For example, the additional parameter area 322 records an Early Warning Score for the patient. The user selects between Scores 1-3. The additional parameter areas 324, 326, capture other parameters, such as CRT, Pain, Respirations, White Cell Count, Respiratory Distress, and/or Conscious Level. While three additional parameters are shown, more or fewer can be captured. For example, the additional parameters that are obtained can be tailored to the vital signs information that is captured by the device and shown on the interface 320.

Figure 11:
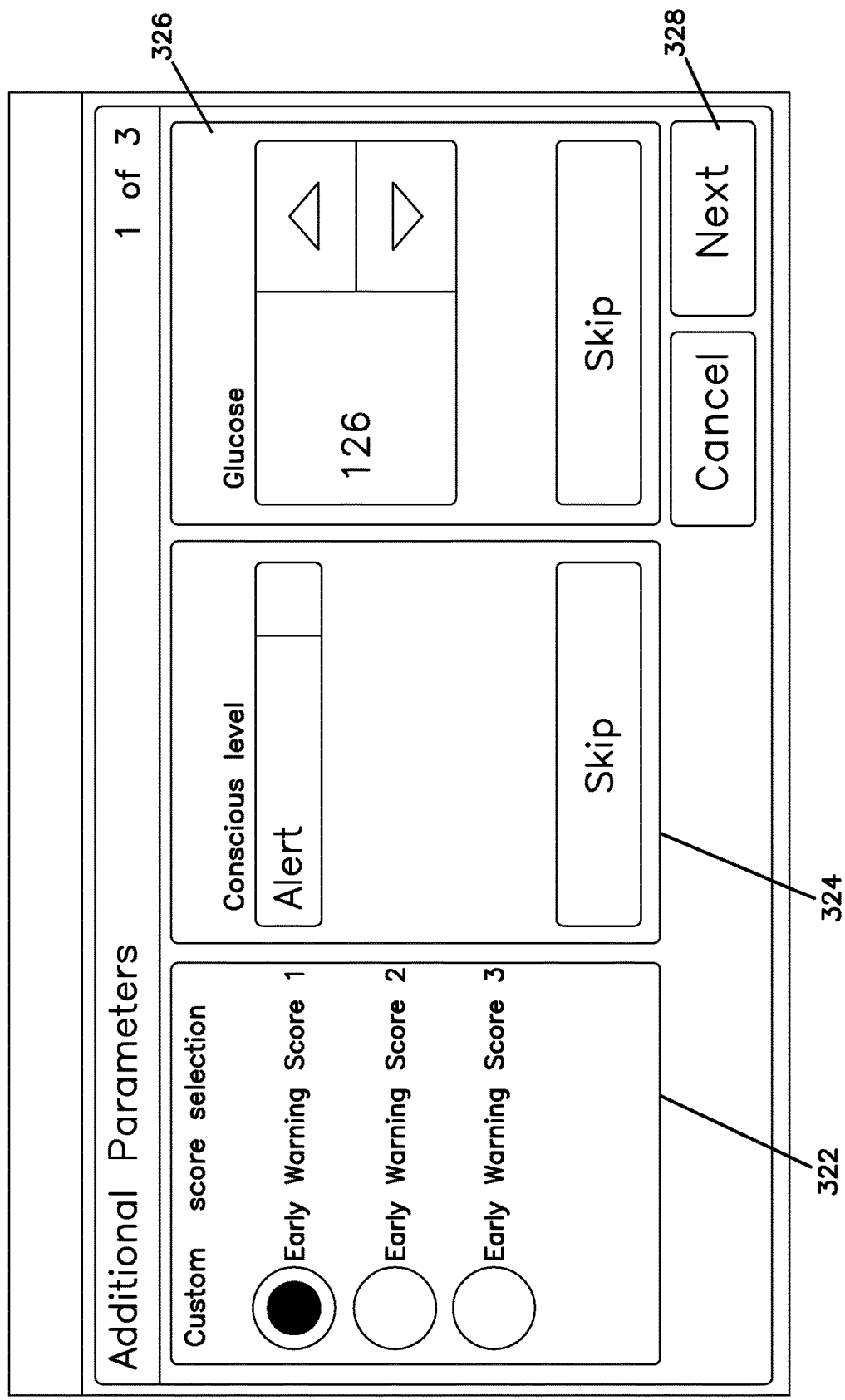
FIG. 11 illustrates another view of the interface of FIG. 9.

Once the user provides the information required in each of the additional parameters areas 322, 324, 326, the next button 328 become active, as shown in FIG. 11. In this example, the user must provide each additional parameter or affirmatively skip one or more of the parameters (see FIG. 14) before the next button 328 become active.

Once the next button 328 is selected, a summary of the additional parameters is provided to the user on an interface 332 at FIG. 12. This allows the user to review the additional parameter information for accuracy. Assuming everything is correct, the user can select the button 330 to store the additional parameters.

Figure 13:
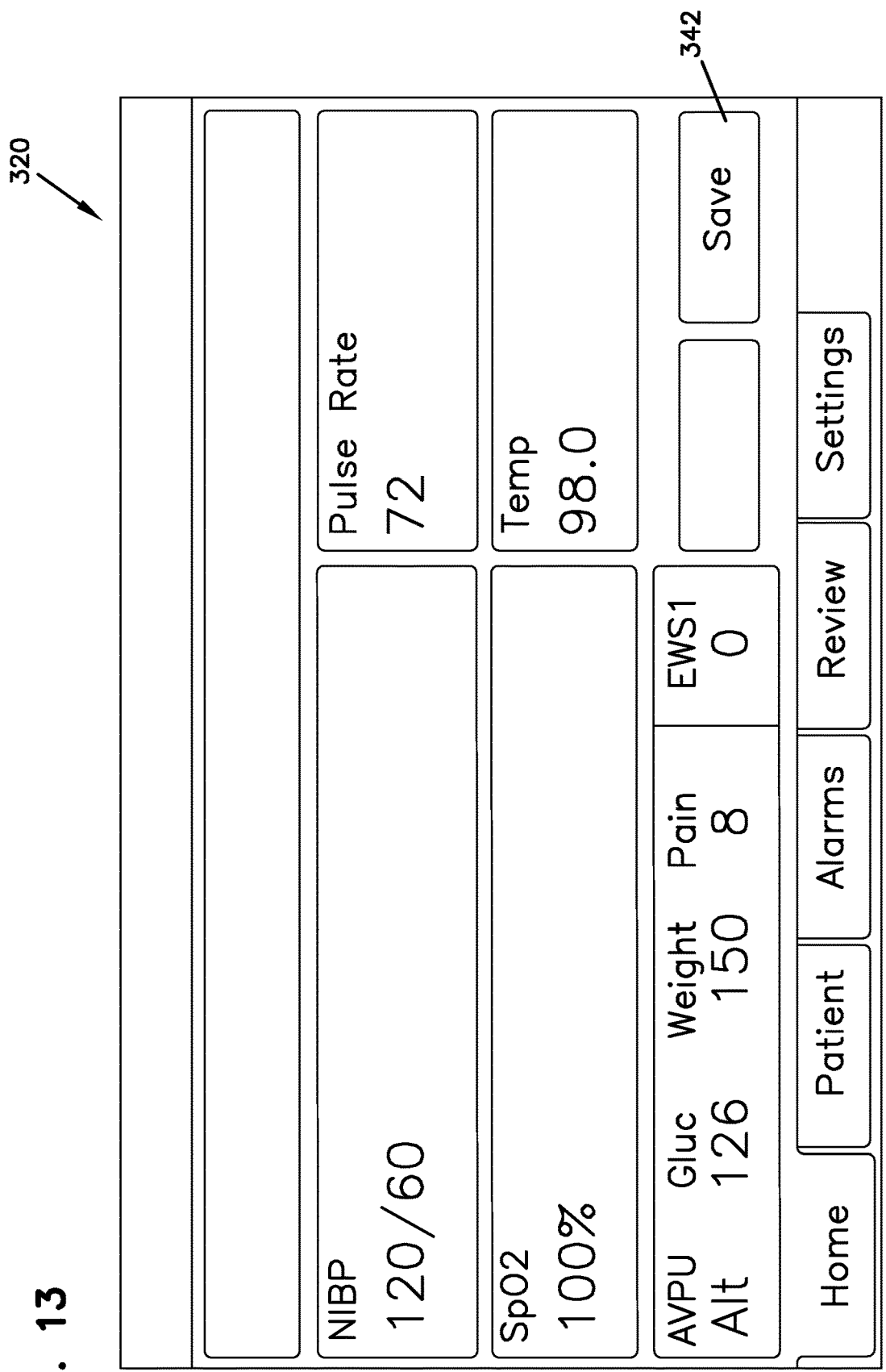
FIG. 13 illustrates another view of the interface of FIG. 9.
Figure 14:
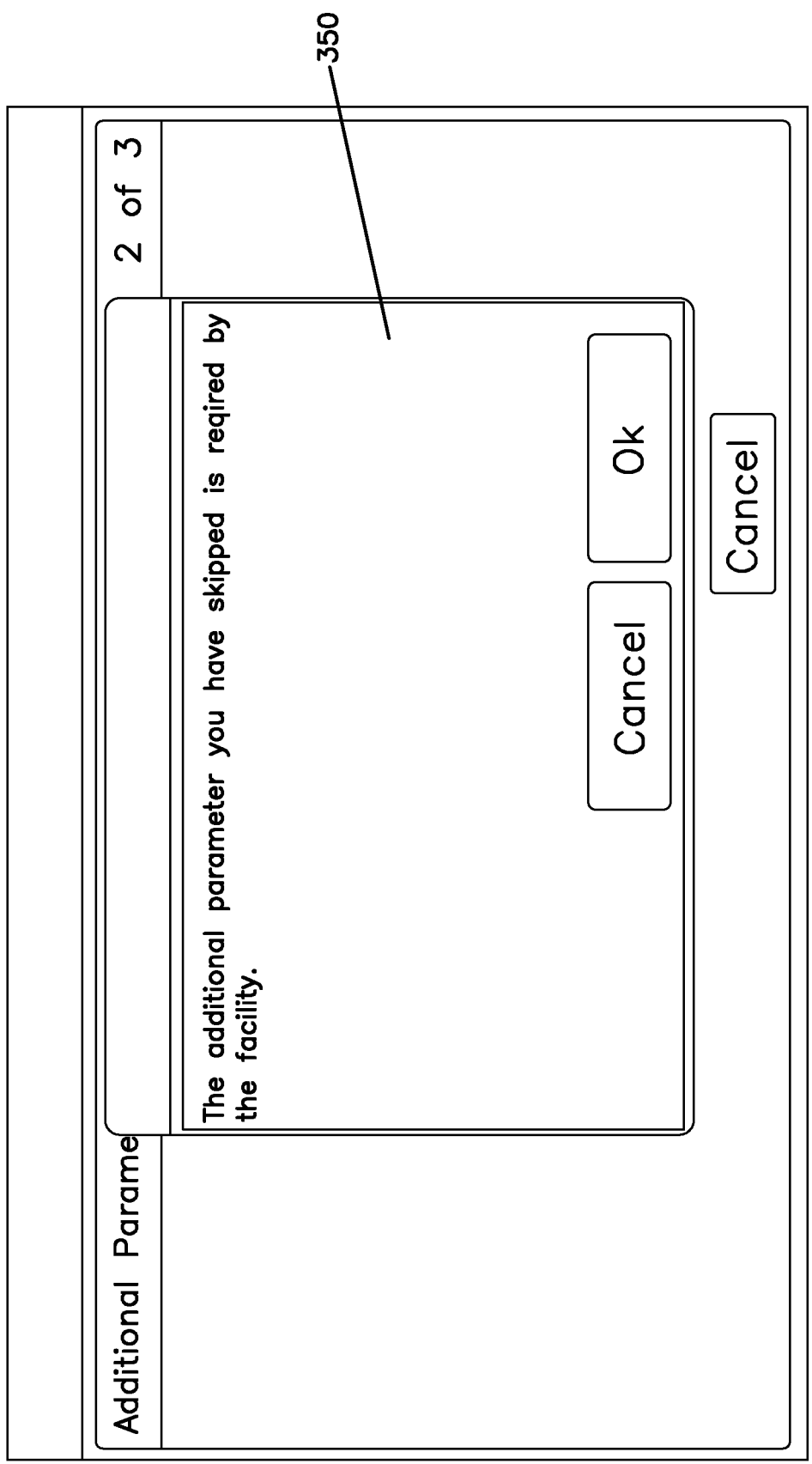
FIG. 14 illustrates another view of the interface of FIG. 9.

At FIG. 13, the interface 320 is again shown. In this context, the next button 328 is removed, and a save button 342 is provided. Once selected by the user, the save button 342 causes the vital signs data and additional parameters to be saved, for example, locally and/or to an EMR record across the network 110.

Referring again to FIGS. 10-11, the additional parameter areas 322, 324, 326 can also include skip buttons that allow the user to avoid providing one or more of the additional parameters. If a skip button is pressed, the user is presented with an interface 350 shown in FIG. 14. The example interface 350 indicates that the particular facility requires that the additional parameter be recorded. If the user selects the "OK" button, recordation of the parameter is overridden, and the override is recorded (e.g., such information as user name and time). If the user selects "Cancel", the user has the opportunity to provide the additional parameter on the appropriate area 322, 324, 326.

In these examples, whether or not the additional parameters are required can be configured based upon device and/or facility preferences. For example, a facility can decide which additional parameters must be captured for certain vital signs data recordations. These parameters can be required before the user is allowed to record the information in the EMR. In other examples, the information can be recorded even if one or more of the additional parameters are skipped. Other configurations are possible.

Figure 15:
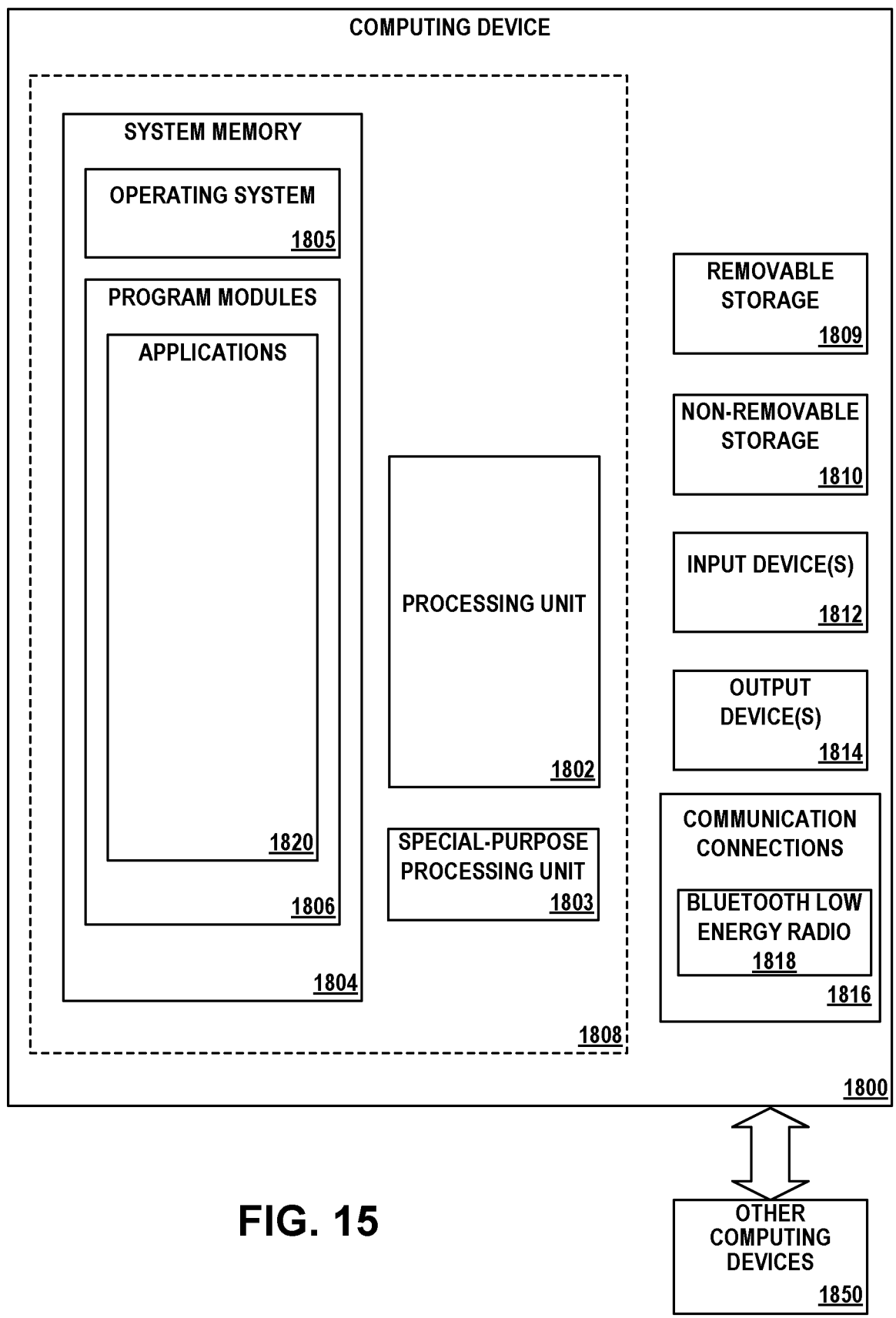
FIG. 15 is a block diagram illustrating physical components of a computing device with which examples and embodiments of the disclosure can be practiced.

FIG. 15 is a block diagram illustrating physical components (i.e., hardware) of a computing device 1800 with which embodiments of the disclosure may be practiced. The computing device components described below may be suitable to act as the computing devices described above, such as wireless computing device and/or medical device of FIG. 1. In a basic configuration, the computing device 1800 may include at least one processing unit 1802 and a system memory 1804. Depending on the configuration and type of computing device, the system memory 1804 may comprise, but is not limited to, volatile storage (e.g., random access memory), non-volatile storage (e.g., read-only memory), flash memory, or any combination of such memories. The system memory 1804 may include an operating system 1805 and one or more program modules 1806 suitable for running software applications 1820. The operating system 1805, for example, may be suitable for controlling the operation of the computing device 1800. Furthermore, embodiments of the disclosure may be practiced in conjunction with a graphics library, other operating systems, or any other application program and is not limited to any particular application or system. This basic configuration is illustrated in FIG. 15 by those components within a dashed line 1808. The computing device 1800 may have additional features or functionality. For example, the computing device 1800 may also include additional data storage devices (removable and/or non-removable) such as, for example, magnetic disks, optical disks, or tape. Such additional storage is illustrated in FIG. 15 by a removable storage device 1809 and a non-removable storage device 1810.

Other program modules that may be used in accordance with embodiments of the present disclosure, and in particular to generate screen content, may include electronic mail and contacts applications, word processing applications, spreadsheet applications, database applications, slide presentation applications, drawing or computer-aided application programs, etc.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. For example, embodiments of the disclosure may be practiced via a system-on-a-chip (SOC) where each or many of the components illustrated in FIG. 15 may be integrated onto a single integrated circuit. Such an SOC device may include one or more processing units, graphics units, communications units, system virtualization units and various application functionality all of which are integrated (or "burned") onto the chip substrate as a single integrated circuit. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general purpose computer or in any other circuits or systems.

The computing device 1800 may also have one or more input device(s) 1812 such as a keyboard, a mouse, a pen, a sound or voice input device, a touch or swipe input device, etc. The output device(s) 1814 such as a display, speakers, a printer, etc. may also be included. The aforementioned devices are examples and others may be used. The computing device 1800 may include one or more communication connections 1816 allowing communications with other computing devices 1818. Examples of suitable communication connections 1816 include, but are not limited to, RF transmitter, receiver, and/or transceiver circuitry; universal serial bus (USB), parallel, and/or serial ports. Additionally, the communication connections 1816 can include a Bluetooth Low Energy Radio.

The term computer readable media as used herein may include non-transitory computer storage media. Computer storage media may include volatile and nonvolatile, removable and non-removable media implemented in any method or technology for storage of information, such as computer readable instructions, data structures, or program modules. The system memory 1804, the removable storage device 1809, and the non-removable storage device 1810 are all computer storage media examples (i.e., memory storage.) Computer storage media may include RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other article of manufacture which can be used to store information and which can be accessed by the computing device 1800. Any such computer storage media may be part of the computing device 1800. Computer storage media does not include a carrier wave or other propagated or modulated data signal.

Communication media may be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

Embodiments of the present disclosure may be utilized in various distributed computing environments where tasks are performed by remote processing devices that are linked through a communications network in a distributed computing environment.

The logical flows depicted herein are just examples. There may be many variations to these diagrams or the steps (or operations) described therein without departing from the spirit of the disclosure. For instance, the steps may be performed in a differing order, or steps may be added, deleted or modified.

While embodiments have been described, it will be understood that those skilled in the art, both now and in the future, may make various improvements and enhancements can be made.

What is claimed is:

1. A method for displaying information and receiving inputs with a medical device, the method comprising:
    displaying a first interface on a display of the medical device, wherein the first interface comprises:
        a login area including one or more prompts for information identifying a user of the medical device; and
        a profile selection area in an inactive state, the profile selection area including two or more profiles offered by the medical device, wherein each of the profiles comprises a series of tasks to be performed by the user with a particular functionality of the medical device, and a textual string description of the series of tasks for each profile is displayed in the profile selection area;
    receiving user identifying information from the user via the login area;
    confirming the user identifying information;
    activating the profile selection area in response to confirming the user identifying information;
    receiving a profile selection from the user via the profile selection area;
    receiving patient identification information for a patient from the user with the medical device in accordance with the series of tasks of the selected profile;
    upon receiving the profile selection and the patient identification information, displaying a second interface on the display of the medical device;
    activating at least one function of the medical device in accordance with the selected profile;
    receiving vital signs data from the patient using the second interface in accordance with the series of tasks of the selected profile;
    upon receiving the vital signs data, displaying a third interface on the display of the medical device, the third interface presenting additional parameter areas prompting the user for additional data for parameters associated with the vitals sign data, and the third interface presenting a skip button for at least one of the additional parameter areas and a next button in an inactive state; and
    upon receiving, for each additional parameter, the additional data or an affirmative indication to skip the parameter by selecting the skip button, activating the next button on the third interface, wherein the affirmative indication to skip the parameter includes receiving selection of a skip button for at least one of the additional parameter areas presented on the third interface, displaying a fourth interface indicating that a corresponding additional parameter is required upon receiving selection of the skip button, receiving selection of a confirmation button presented on the fourth interface, and recording an override of the required additional parameter upon receiving selection of the confirmation button, the record of the override including at least a username of the user and a time.

2. The method of claim 1, wherein displaying the login area of the first interface comprises displaying at least one prompt selected from a clinician identifier, a password, a user name and a badge number.

3. The method of claim 1, wherein receiving user identifying information comprises receiving the identifying information entered by the user using an input device selected from a touchscreen, a keyboard, a mouse and a scanner.

4. The method of claim 1, wherein the user identifying information must be confirmed before the user can select one of the two or more profiles in the profile selection area.

5. The method of claim 1, wherein the medical device confirms the identifying information locally, at the medical device.

6. The method of claim 1, wherein the two or more profiles of the displayed profile selection area comprise:
   a spot profile;
   an office profile; and
   an interval profile.

7. The method of claim 1, wherein the description in the profile selection area for each of the two or more profiles includes a series of sentences providing a prose description of a functionality associated with each respective profile.

8. The method of claim 1, further comprising displaying a patient identification box on the display of the medical device, after receiving the profile selection from the user, to prompt the user to input the patient identification information.

9. The method of claim 1, wherein displaying the first interface further comprises displaying a control that, when selected, allows the user to use the medical device with limited functionality without providing login credentials to capture vital signs data in an emergency situation.

10. A method for displaying information and receiving inputs with a medical device, the method comprising:
   displaying a first interface on a display of the medical device, wherein the first interface comprises:
      a login area including one or more prompts for information identifying a user of the medical device; and
      a profile selection area in an inactive state, the profile selection area including two or more profiles offered by the medical device, wherein each of the profiles comprises a series of tasks to be performed by the user with a particular functionality of the medical device, and a textual string description of what is accomplished with each profile is displayed in the profile selection area;
   receiving and confirming user identifying information;
   activating the profile selection area in response to confirming the user identifying information;
   receiving, at the profile selection area in an active state, a profile selection;
   receiving patient identification information from the user of the medical device;
   upon receiving the profile selection and the patient identification information, displaying a second interface on the display of the medical device, wherein the second interface is configured to capture vital signs data of a patient and includes a first next button in an inactive state;
   activating at least one function of the medical device in accordance with the selected profile;
   receiving vital signs data from the patient using the second interface in accordance with the selected profile;
   activating the first next button;
   receiving a selection of the first next button; and
   displaying a third interface on the display, wherein the third interface includes multiple additional parameter areas, a skip button for at least one of the additional parameter areas, and a second next button in an inactive state, and wherein the multiple additional parameter areas are configured to capture one or more additional parameters associated with the vital signs data captured with the second interface; and
   upon receiving the additional data or an indication to skip for each additional parameter, activating the second next button on the third interface, wherein the affirmative indication to skip the parameter includes receiving selection of a skip button for at least one of the additional parameter areas presented on the third interface, displaying a fourth interface indicating that a corresponding additional parameter is required upon receiving selection of the skip button, receiving selection of a confirmation button presented on the fourth interface, and recording an override of the required additional parameter upon receiving selection of the confirmation button, the record of the override including at least a username of the user and a time.

11. The method of claim 10, wherein the identifying information must be confirmed before the user can select one of the two or more profiles in the profile selection area.

12. The method of claim 10, wherein one of the multiple additional parameter areas of the third interface records an early warning score for the patient.

13. The method of claim 10, wherein the additional parameter areas include multiple separate areas, and wherein each of the multiple separate areas is configured to capture one of the additional parameters.

14. The method of claim 10, further comprising activating a control used to save data associated with recorded vital signs data and the additional parameters when the user provides the additional parameters.

15. The method of claim 10, wherein the two or more profiles of the displayed profile selection area comprise:
   a spot profile;
   an office profile; and
   an interval profile.

16. The method of claim 10, wherein the description in the profile selection area for each of the two or more profiles includes a series of sentences providing a prose description of a functionality associated with each respective profile.

* * * * *